US008986383B2

(12) United States Patent
Castro (10) Patent No.: US 8,986,383 B2
(45) Date of Patent: Mar. 24, 2015

(54) END CAP AND CONNECTOR FOR A SPINAL IMPLANT

(75) Inventor: Frank Castro, Louisville, KY (US)

(73) Assignee: IGIP, LLC, Louisville, KY (US)

( * ) Notice: Subject to any disclaimer, the term of this patent is extended or adjusted under 35 U.S.C. 154(b) by 413 days.

(21) Appl. No.: 13/199,418

(22) Filed: Aug. 30, 2011

(65) Prior Publication Data

US 2012/0004730 A1    Jan. 5, 2012

Related U.S. Application Data (63) Continuation-in-part of application No. 12/804,867, filed on Jul. 30, 2010, now Pat. No. 8,673,006, which is a continuation-in-part of application No. 12/583,865, filed on Aug. 27, 2009, now Pat. No. 8,246,683, which is a continuation-in-part of application No. 12/290,069, filed on Oct. 27, 2008, now Pat. No. 8,226,718, which is a continuation-in-part of application No. 12/221,779, filed on Aug. 6, 2008, now Pat. No. 8,002,832, which is a continuation of application No. 11/089,103, filed on Mar. 24, 2005, now Pat. No. 7,435,261, said application No. 12/804,867 is a continuation-in-part of application No. 12/583,864, filed on Aug. 27, 2009, now Pat. No. 8,361,149, which is a continuation-in-part of application No. 12/290,069.

(51) Int. Cl.
*A61F 2/44* (2006.01)
*A61F 2/30* (2006.01)

(52) U.S. Cl.
CPC . *A61F 2/44* (2013.01); *A61F 2/447* (2013.01); *A61F 2/30744* (2013.01); *A61F 2002/30032* (2013.01); *A61F 2002/30062* (2013.01); *A61F 2002/30158* (2013.01); *A61F 2002/30271* (2013.01); *A61F 2002/30354* (2013.01); *A61F 2002/30481* (2013.01); *A61F 2002/30578* (2013.01); *A61F 2002/30604* (2013.01); *A61F 2210/0004* (2013.01); *A61F 2220/0025* (2013.01); *A61F 2220/0033* (2013.01); *A61F 2230/0026* (2013.01); *A61F 2230/0082* (2013.01); *A61F 2250/003* (2013.01); *A61F 2310/00017* (2013.01); *A61F 2310/00023* (2013.01)
USPC .................................................. 623/17.11

(58) Field of Classification Search
CPC ...................................................... A61F 2/447
USPC ........................................... 623/17.11–17.16
See application file for complete search history.

(56) References Cited

U.S. PATENT DOCUMENTS

| | | |
|---|---|---|
| 5,147,402 A | 9/1992 | Bohler et al. |
| 5,192,327 A | 3/1993 | Brantigan |

(Continued)

FOREIGN PATENT DOCUMENTS

GB    2364643    2/2002

OTHER PUBLICATIONS

Barack, R. L. Revision Totatl Hip Arthroplasty: The Femoral Component. J. Am Acad Orthop Surg 1995; 3(2); 79-85. USA.

(Continued)

*Primary Examiner* — Eduardo C Robert
*Assistant Examiner* — Stuart S Bray
(74) *Attorney, Agent, or Firm* — Kenneth F. Pearce (57) ABSTRACT

The present invention is a spinal implant that can be inserted into a surgically created cavity of one or more regions of the mammalian spine. Among other things, the biocompatible implant and end cap or biocompatible implant, connector and end cap combinations can assist with the restoration of the normal anatomic spinal alignment and spinal stability.

18 Claims, 6 Drawing Sheets

(56) References Cited

U.S. PATENT DOCUMENTS

| | | | |
|---|---|---|---|
| 5,425,772 A | 6/1995 | Brantigan | |
| 5,458,638 A | 10/1995 | Kuslich et al. | |
| 5,558,674 A | 9/1996 | Heggeness et al. | |
| 5,609,635 A | 3/1997 | Michelson | |
| 5,766,252 A | 6/1998 | Henry et al. | |
| 5,888,228 A | 3/1999 | Knothe et al. | |
| 5,968,098 A | 10/1999 | Winslow | |
| 5,980,522 A | 11/1999 | Koros et al. | |
| 6,066,175 A | 5/2000 | Henderson et al. | |
| 6,080,193 A | 6/2000 | Hochshuler et al. | |
| 6,090,143 A | 7/2000 | Meriwether et al. | |
| 6,117,174 A | 9/2000 | Nolan | |
| 6,159,244 A * | 12/2000 | Suddaby | 623/17.11 |
| 6,159,245 A | 12/2000 | Meriwether et al. | |
| 6,231,610 B1 | 5/2001 | Geisler | |
| 6,287,343 B1 | 9/2001 | Kuslich et al. | |
| 6,302,914 B1 * | 10/2001 | Michelson | 623/17.16 |
| 6,395,030 B1 * | 5/2002 | Songer et al. | 623/17.11 |
| 6,395,035 B2 | 5/2002 | Bresina et al. | |
| 6,409,766 B1 | 6/2002 | Brett | |
| 6,432,107 B1 * | 8/2002 | Ferree | 606/247 |
| 6,491,724 B1 | 12/2002 | Ferree | |
| 6,537,320 B1 | 3/2003 | Michelson | |
| 6,562,074 B2 * | 5/2003 | Gerbec et al. | 623/17.15 |
| 6,569,201 B2 * | 5/2003 | Moumene et al. | 623/17.11 |
| 6,576,016 B1 | 6/2003 | Hochshuler et al. | |
| 6,582,432 B1 | 6/2003 | Michelson | |
| 6,613,091 B1 | 9/2003 | Zdeblick et al. | |
| 6,641,614 B1 | 11/2003 | Wagner et al. | |
| 6,648,917 B2 | 11/2003 | Gerbec et al. | |
| 6,660,038 B2 | 12/2003 | Boyer et al. | |
| 6,712,825 B2 | 3/2004 | Aebi et al. | |
| 6,712,852 B1 | 3/2004 | Chung et al. | |
| 6,746,484 B1 | 6/2004 | Liu et al. | |
| 6,761,738 B1 | 7/2004 | Boyd | |
| 6,767,367 B1 | 7/2004 | Michelson | |
| 6,776,798 B2 * | 8/2004 | Camino et al. | 623/17.16 |
| 6,805,714 B2 * | 10/2004 | Sutcliffe | 623/17.11 |
| 6,808,538 B2 * | 10/2004 | Paponneau | 623/17.16 |
| 6,837,905 B1 * | 1/2005 | Lieberman | 623/17.16 |
| 6,852,129 B2 | 2/2005 | Gerbec et al. | |
| 6,863,673 B2 | 3/2005 | Gerbec et al. | |
| 6,926,737 B2 | 8/2005 | Jackson et al. | |
| 6,929,662 B1 | 8/2005 | Messerli et al. | |
| 6,942,697 B2 | 9/2005 | Lange et al. | |
| 6,997,953 B2 | 2/2006 | Chung et al. | |
| D524,942 S * | 7/2006 | Felix | D24/155 |
| 7,166,110 B2 | 1/2007 | Yundt | |
| 7,182,782 B2 | 2/2007 | Kirschman | |
| 7,232,463 B2 * | 6/2007 | Falahee | 623/17.11 |
| 7,435,261 B1 * | 10/2008 | Castro | 623/17.11 |
| 7,594,931 B2 * | 9/2009 | Louis et al. | 623/17.11 |
| 7,618,460 B2 * | 11/2009 | Boyd | 623/17.16 |
| 7,621,953 B2 | 11/2009 | Braddock, Jr. et al. | |
| 7,641,701 B2 | 1/2010 | Kirschman | |
| 7,942,932 B2 * | 5/2011 | Castro | 623/17.11 |
| 8,002,832 B2 * | 8/2011 | Castro | 623/17.11 |
| 8,016,887 B1 * | 9/2011 | Castro | 623/17.11 |
| 8,226,718 B2 * | 7/2012 | Castro | 623/17.11 |
| 8,246,683 B2 * | 8/2012 | Castro | 623/17.11 |
| 8,361,149 B2 * | 1/2013 | Castro | 623/17.11 |
| 8,491,653 B2 * | 7/2013 | Zucherman et al. | 623/17.11 |
| 2002/0099443 A1 | 7/2002 | Messerli et al. | |
| 2002/0128652 A1 * | 9/2002 | Ferree | 606/61 |
| 2002/0138142 A1 * | 9/2002 | Castro et al. | 623/17.11 |
| 2003/0125739 A1 | 7/2003 | Bagga et al. | |
| 2003/0199980 A1 * | 10/2003 | Siedler | 623/17.11 |
| 2004/0064184 A1 | 4/2004 | Chung et al. | |
| 2004/0073314 A1 * | 4/2004 | White et al. | 623/17.15 |
| 2004/0126407 A1 | 7/2004 | Falahee | |
| 2004/0153155 A1 * | 8/2004 | Chung et al. | 623/17.11 |
| 2004/0153160 A1 * | 8/2004 | Carrasco | 623/17.15 |
| 2004/0176842 A1 * | 9/2004 | Middleton | 623/17.13 |
| 2004/0199254 A1 * | 10/2004 | Louis et al. | 623/17.11 |
| 2004/0204714 A1 | 10/2004 | Liu et al. | |
| 2004/0225360 A1 * | 11/2004 | Malone | 623/17.11 |
| 2005/0071006 A1 * | 3/2005 | Kirschman | 623/17.11 |
| 2005/0071008 A1 * | 3/2005 | Kirschman | 623/17.11 |
| 2005/0149192 A1 * | 7/2005 | Zucherman et al. | 623/17.11 |
| 2005/0159813 A1 | 7/2005 | Molz, IV et al. | |
| 2005/0187630 A1 * | 8/2005 | Castro et al. | 623/17.11 |
| 2006/0058879 A1 * | 3/2006 | Metz-Stavenhagen | 623/17.15 |
| 2006/0178752 A1 | 8/2006 | Yaccarino, III et al. | |
| 2006/0235406 A1 | 10/2006 | Silverman | |
| 2006/0287725 A1 * | 12/2006 | Miller | 623/17.11 |
| 2007/0016295 A1 | 1/2007 | Boyd | |
| 2007/0123987 A1 * | 5/2007 | Bernstein | 623/17.11 |
| 2007/0129805 A1 * | 6/2007 | Braddock et al. | 623/17.11 |
| 2007/0250167 A1 | 10/2007 | Bray et al. | |
| 2007/0255409 A1 | 11/2007 | Dickson et al. | |
| 2007/0255413 A1 * | 11/2007 | Edie et al. | 623/17.16 |
| 2008/0015694 A1 | 1/2008 | Tribus | |
| 2008/0021476 A1 * | 1/2008 | Kirschman | 606/69 |
| 2008/0114454 A1 * | 5/2008 | Peterman et al. | 623/17.16 |
| 2008/0132901 A1 | 6/2008 | Recoules-arche et al. | |
| 2008/0275506 A1 | 11/2008 | Baynham et al. | |
| 2009/0036985 A1 * | 2/2009 | Whiting | 623/17.11 |
| 2009/0138083 A1 * | 5/2009 | Biyani | 623/17.11 |
| 2009/0234364 A1 | 9/2009 | Crook | |
| 2010/0004752 A1 | 1/2010 | White et al. | |
| 2010/0305701 A1 * | 12/2010 | Castro | 623/17.11 |
| 2010/0324678 A1 * | 12/2010 | Castro | 623/17.11 |
| 2010/0324679 A1 * | 12/2010 | Castro | 623/17.11 |
| 2010/0324681 A1 * | 12/2010 | Castro | 623/17.11 |
| 2010/0324682 A1 * | 12/2010 | Castro | 623/17.11 |
| 2010/0324685 A1 * | 12/2010 | Castro | 623/17.16 |
| 2011/0029081 A1 * | 2/2011 | Malone | 623/17.11 |
| 2012/0004730 A1 * | 1/2012 | Castro | 623/17.16 |

OTHER PUBLICATIONS

Castro, F. P., Jr. Stingers, Cervical Cord Neurapraxia, and Stenois. Clin Sport Med 2003; 22: 483-492. USA.

Majd M.E., Vadhva, M., Holt R.T. Anterior Cervical Reconstruction Using Titanium Cages With Anterior Plating. Spine 1999; 24 (15): 1604-1610. USA.

Park J.B., Cho Y.S., Riew, K.D. Development of Adjacent-Level Ossification in Patient with an Anterior Cervical Plate. J. Bone Surg. 1005; 87-A: 558-563. USA.

* cited by examiner

END CAP AND CONNECTOR FOR A SPINAL IMPLANT

This application is a Continuation-in-Part of application for Letters Patent Ser. No. 12/804,867 entitled—Spinal Implant—filed on Jul. 30, 2010 now U.S. Pat. No. 8,673,006 that is a Continuation-In-Part of applications for Letters Patent Ser. No. 12/583,865 entitled—Spinal Implant—filed on Aug. 27, 2009 now U.S. Pat. No. 8,246,683 and application for Letters Patent Ser. No. 12/583,864 entitled—Wedge-Like Spinal Implant—filed on Aug. 27, 2009 now U.S. Pat. No. 8,361,149, wherein the applications for Letters Patent Ser. No. 12/583,864 and Ser. No. 12/583,865 are Continuations-In-Part of application for Letters Patent, Ser. No. 12/290,069, entitled—Spinal Implant and Method of Using Spinal Implant—filed on Oct. 27, 2008 now U.S. Pat. No. 8,226,718 that is a Continuation-In-Part of application for Letters Patent, Ser. No. 12/221,779 entitled—Spinal Implant and Method of Using Spinal Implant—filed on Aug. 6, 2008 now U.S. Pat. No. 8,002,832 that is a Continuation of application for Letters Patent, Ser. No. 11/089,103 entitled—Spinal Implant and Method of Using Spinal Implant—filed on Mar. 24, 2005, now U.S. Pat. No. 7,435,261 B2 issued on Oct. 14, 2008.

BACKGROUND OF THE INVENTION

A. Field of the Invention

Among other things, the present invention is related to a surgical implant or a biocompatible cage and end cap combination or biocompatible cage end cap and connector combination that can be inserted into a cavity that has been created by removing spinal tissue. Post operative and prior to complete arthrodesis, the current invention inhibits extrusion of the cage against the spinal cord. Inclusion of a connector between the biocompatible implant and the end cap allows the spinal column to be distracted a greater length than the length of the biocompatible implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) US Published Patent Application No. 20030125739 A1—Bagga, et al. discloses a bioactive spinal implant and method of manufacture. Among other things, it does not appear that the Bagga invention practices the use of a cage having a trapezoidal divider, an end cap with docking slides and plate including an opening or a connector positioned between the cage and the end cap.

2) U.S. Pat. No. 6,767,367—Michelson enables a spinal fusion implant having deployable bone engaging projections. Michelson teaches that the '367 implant 300 has a rotatable member 320 that is preferably frustoconical in shape. Among other things, it does not appear that the Michelson invention practices the use of a cage having a trapezoidal divider, an end cap with docking slides and plate including an opening or a connector positioned between the cage and the end cap.

3) U.S. Pat. No. 6,537,320—Michelson enables a self-broaching, rotable, push-in interbody spinal fusion implant and method for its deployment. Among other things, it does not appear that the Michelson invention practices the use of a cage having a trapezoidal divider, an end cap with docking slides and plate including an opening or a connector positioned between the cage and the end cap.

4) U.S. Pat. No. 5,609,635—Michelson enables a lordotic interbody spinal fusion implant. The Michelson Summary of the Invention teaches, "In the preferred embodiment of the modular implant, the implant is again wedge-shaped in the side elevational view and is taller at its insertion end than at its trailing end." Being taller at an insertion end than at the trailing end is a teaching that is incompatible with the current spinal implant. Further, among other things, it does not appear that the Michelson invention practices the use of a cage having a trapezoidal divider, an end cap with docking slides and plate including an opening or a connector positioned between the cage and the end cap.

5) U.S. Pat. No. 6,302,914—Michelson enables a lordotic interbody spinal fusion implant. The '914 patent is a continuation of U.S. Pat. No. 5,609,635—Michelson patent and enables the same limitations as the '635 patent.

6) U.S. Pat. No. 6,066,175—Henderson, et al. enables a fusion stabilization chamber. Henderson discloses a mesh cage 41, barrel vaults 48 and 49 and flanges 50 and 51 to anchor the cage. The cage is preferably rectangular when viewed from the top or the bottom. Among other things, it does not appear that the Henderson invention practices the use of a cage having a trapezoidal divider, an end cap with docking slides and plate including an opening or a connector positioned between the cage and the end cap.

7) U.S. Pat. No. 5,766,252—Henry, et al. enables an interbody spinal prosthetic implant and method. Henry requires a threaded hole 38 to practice the '252 invention. Among other things, it does not appear that the Henry invention practices the use of a cage having a trapezoidal divider, an end cap with docking slides and plate including an opening or a connector positioned between the cage and the end cap.

8) U.S. Pat. No. 5,425,772—Brantigan enables a prosthetic implant for intervertibral spinal fusion. The '772 device practices traverse teeth or serrations 19 where the teeth have sharp peaks 19a, slopping walls 19b and valleys 19c. Among other things, it does not appear that the Brantigan invention practices the use of a cage having a trapezoidal divider, an end cap with docking slides and plate including an opening or a connector positioned between the cage and the end cap.

9) U.S. Pat. No. 5,147,402—Bohler, et al. enables an implant for ingrowth of osseous tissue. Among other things, it does not appear that the Bohler invention practices the use of a cage having a trapezoidal divider, an end cap with docking slides and plate including an opening or a connector positioned between the cage and the end cap.

10) U.S. Pat. No. 6,746,484—Liu, et al. enables a spinal implant. Among other things, Liu teaches an implant 1 having an elongate hollow body 3, parallel longitudinal walls 4 and terminal ends 5 and 6 including threaded holes 11a. Among other things, it does not appear that the Liu invention practices the use of a cage having a trapezoidal divider, an end cap with docking slides and plate including an opening or a connector positioned between the cage and the end cap.

11) U.S. Pat. No. 6,231,610—Geisler enables an anterior cervical column support device. The '610 apparatus utilizes serrations on the load bearing surfaces and two screw holes. Among other things, it does not appear that the Geisler invention practices the use of a cage having a trapezoidal divider, an end cap with docking slides and plate including an opening or a connector positioned between the cage and the end cap.

12) U.S. Pat. No. 6,660,038—Boyer, et al. enables skeletal reconstruction cages. The Boyer Patent discloses an end cap 210 suitable for coupling to central shaft 160 includes an outer wall 212, as well as a central hole disposed along axis 213 with a lower inner wall 214, an upper inner wall 216, and an inner ridge portion 218. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160. Among other things, it does not appear that the Boyer invention practices the use of a cage having a trapezoidal divider, an end cap with docking slides and plate including an opening or a connector positioned between the cage and the end cap.

13) U.S. Pat. No. 6,491,724—Ferree enables a spinal fusion cage with lordosis correction. Ferree teaches an anterior portion 112 that includes mating members 120 and 122 with teeth 124 or other features to form a locking or ratchet mechanism that is used to alter the height of the cage. Among other things, it does not appear that the Ferree invention practices the use of a cage having a trapezoidal divider, an end cap with docking slides and plate including an opening or a connector positioned between the cage and the end cap.

14) U.S. Pat. No. 6,117,174—Nolan enables a spinal implant device that has disc 14 made of the same material as body 12. Among other things, it does not appear that the Nolan invention practices the use of a cage having a trapezoidal divider, an end cap with docking slides and plate including an opening or a connector positioned between the cage and the end cap.

15) US Published Patent Application No. 20070016295—Boyd discloses a reinforced molded implant formed of cortical bone. Boyd reads, "Implant 10 defines a longitudinal axis 11 and includes a first strut 12, a second strut 14 spaced from first strut 12, and cross-member 16 extending therebetween. First strut 12 and second strut 14 are each positioned to lie in a plane substantially parallel to longitudinal axis 11. Implant 10 includes at least one additional cross-member 16 A connecting first strut 12 and second strut 14." Among other things, it does not appear that the Boyd invention practices the use of a cage having a trapezoidal divider, an end cap with docking slides and plate including an opening or a connector positioned between the cage and the end cap.

16) U.S. Pat. No. 6,090,143—Meriwether, et al. enables a box cage for intervertebral body fusion. Meriwether reads, "The assembled cage comprises a box-like base 112 and a cover 114 dimensioned to fit over the base much like the cover on a shirt box. The height dimension of the rightmost ends of the base and cover are greater than the height dimension of the corresponding, opposed left side ends, thus providing the desired wedge shape. Upwardly projecting ribs 116 and 118 extend along the rear and front side edges, respectfully, and likewise, the base 112 includes longitudinally extending ribs 120 and 122 projecting downwardly from the undersurface of the base along the side edges thereof. The right and left ends of the base 112 and the cover 114 include semi-circular cutouts as at 124 and 126 and 128-130 such that when the cover 114 is placed upon the base 112, circular apertures are formed. These apertures are adapted to receive a tapered screw 132 therein." Among other things, it does not appear that the Meriwether invention practices the use of a cage having a trapezoidal divider, an end cap with docking slides and plate including an opening or a connector positioned between the cage and the end cap.

17) U.S. Pat. No. 6,159,245—Meriwether, et al. enables a box cage for intervertebral body fusion. The '245 Meriwether Patent is a continuation of U.S. Pat. No. 6,090,143—Meriwether, et al. and teaches the same limitations as the '143 patent.

18) U.S. Pat. No. 6,432,107—Ferree enables enhanced surface area spinal fusion devices. The '107 patent teaches, "The device 200 fits into slots 204 and 206 made in upper and lower vertebrae 208 and 210, respectively, allowing the lower section to fuse within the body of the lower vertebrae 210, and the upper section to fuse within the body of the upper vertebrae 208." Among other things, it does not appear that the Ferree invention practices the use of a cage having a trapezoidal divider, an end cap with docking slides and plate including an opening or a connector positioned between the cage and the end cap.

19) U.S. Pat. No. 6,569,201—Moumene, et al. enables a hybrid composite interbody fusion device. Among other things, it does not appear that the Moumene invention practices the use of a cage having a trapezoidal divider, an end cap with docking slides and plate including an opening or a connector positioned between the cage and the end cap.

20) U.S. Pat. No. 6,576,016—Hochshuler, et al. enables an adjustable height fusion device. The '016 patent discloses, "Fusion device 10 preferably includes a pair of sides or engaging plates 12 and 14 for engaging vertebral bodies 16 and 18. The engaging plates may contain curved edges such that the outer face 15 of the plates conforms to the shape of the cross-section of the vertebral bodies as shown in FIG. 3." Among other things, it does not appear that the Hochshuler invention practices the use of a cage having a trapezoidal divider, an end cap with docking slides and plate including an opening or a connector positioned between the cage and the end cap.

21) U.S. Pat. No. 6,641,614—Wagner, et al. enables a multi-variable-height fusion device. The '614 patent discloses, "Bracket assembly 206 (depicted in perspective view in FIG. 28) preferably includes an alignment device for changing a height between engaging plates 202 and 204. In an embodiment, the alignment device includes first turnbuckle 250 and second turnbuckle 270 positioned substantially parallel to and substantially adjacent first side edge 212 and second side edge 214, respectively, and extending between anterior edge 208 and posterior edge 210." Among other things, it does not appear that the Wagner invention practices the use of a cage having a trapezoidal divider, an end cap with docking slides and plate including an opening or a connector positioned between the cage and the end cap.

22) U.S. Pat. No. 6,080,193—Hochshuler, et al. enables a multi-variable-height fusion device. The '193 patent discloses, "FIG. 11 depicts a front (anterior) view of the fusion device in a raised position. In an embodiment, the engaging plates include ribs 84 and 85 that may extend substantially perpendicularly from face 15. A cross-sectional view taken along plane III of FIG. 11 is depicted in each of FIG. 12 and FIG. 13. FIG. 12 depicts rib 84 and cam pins 86 and 88 in section with the fusion device in a "lowered position" (i.e., unadjusted for lordotic alignment). FIG. 13 depicts the rib and cam pins in section with the fusion device in the "raised position" (i.e., adjusted for lordotic alignment). As described herein, "cam pin" is taken to mean any connecting element capable of extending from the connector into the slots 90 and 92. Each of the cam pins may be intersected by an imaginary longitudinal axis 91 axially extending through the fusion device." Among other things, it does not appear that the Hochshuler invention practices the use of a cage having a trapezoidal divider, an end cap with docking slides and plate including an opening or a connector positioned between the cage and the end cap.

23) US Published Patent Application No. 20080275506—Baynham, et al. discloses a spinal implant. The '506 Application discloses, "Along the longitudinal periphery of the sidewall 12 is a series of teeth terminating in a sharpened apex. On one portion of the periphery the teeth 24 and 26 are angled away from the small end 14. In the other portion of the periphery of sidewall 12, the teeth 25 and 27 are angled toward the small end wall 14, as shown in FIG. 3. The periphery of sidewall 16 is similarly shaped with the teeth 22 angled away from the small end wall 14 and the teeth 23 angled toward the small end wall 14. The angled teeth gain purchase in the bone and act as a ratchet to prevent relative movement between the implant and the end plates of the adjacent vertebrae." Among other things, it does not appear that the Baynham invention practices the use of a cage having a trapezoidal divider, an end cap with docking slides and plate including an opening or a connector positioned between the cage and the end cap.

24) US Published Patent Application No. 20050159813—Molz IV, et al. discloses a spinal implant construct and method for implantation. The '813 Application discloses, "In one embodiment of the present invention, the cage portion 17 of the fusion construct 16 extends along a longitudinal axis 18 and has a generally rectangular, parallelepiped configuration including front and rear portions 17 F, 17 R, left and right side portions 17 L, 17 P (also referred to as primary portions), and top and bottom portions 17 T, 17 B (also referred to as secondary portions)." Among other things, it does not appear that the Molz invention practices the use of a cage having a trapezoidal divider, an end cap with docking slides and plate including an opening or a connector positioned between the cage and the end cap.

25) U.S. Pat. No. 6,287,343—Kuslich, et al. enables a threaded implant with bone ingrowth openings. The '343 patent discloses, "As shown in those figures, the implant 120 (shown assembled in FIGS. 23 and 25) includes a body portion 122 (shown in perspective in FIGS. 14 and 15) which is generally oval-shaped in cross section and formed from rigid, biocompatible material (preferably titanium). The body 122 includes generally flat side walls 124, 126 joined by upper and lower semi-cylindrical arcuate ribs 128. Arcuate ribs 128 are spaced apart to define a plurality of upper and lower semi-circular arcuate openings 130 which provide communication between a hollow interior 132 of body 122 and an exterior." Among other things, it does not appear that the Kuslich invention practices the use of a cage having a trapezoidal divider, an end cap with docking slides and plate including an opening or a connector positioned between the cage and the end cap.

26) U.S. Pat. No. 6,805,714—Sutcliffe enables an anchorable vertebral implant. The '714 patent discloses, "As seen in FIGS. 1 and 2 an implant 1 according to the invention for installation between a pair of vertebrae 2 has a lower end part 3, and upper end part 4, and a center sleeve or part 5, all made of a biologically inert or absorbable material such as steel, titanium, bone, bioceramic, or polyetherether-ketone (PEEK). The upper part 2 has a downwardly extending externally threaded tubular stem 18 and the lower part 3 has an upwardly extending externally threaded tubular stem 15." Among other things, it does not appear that the Sutcliffe invention practices the use of a cage having a trapezoidal divider, an end cap with docking slides and plate including an opening or a connector positioned between the cage and the end cap.

27) US Published Patent Application No. 20080132901—Recoules-arche, et al. discloses a spinal implant and instrument. The '901 Application discloses, "The cages 2 and 3 have openings 5 extending from bottom to top which can be filled with bone graft material." Among other things, it does not appear that the Recoules-arche invention practices the use of a cage having a trapezoidal divider, an end cap with docking slides and plate including an opening or a connector positioned between the cage and the end cap.

28) US Published Patent Application No. 20090234364—Crook discloses a spinal implant and instrument. The '364 Application teaches, "Thus, the spinal implant device 12 has a rounded prismatic or other suitable shape, and has a thickness on the order of millimeters to centimeters. The spinal implant device 12 includes a draw bar 16 and a pivot bar 18 by which the spinal implant device 12 is grasped and pivoted by and relative to the surgical positioning assembly 10." Among other things, it does not appear that the Crook invention practices the use of a cage having a trapezoidal divider, an end cap with docking slides and plate including an opening or a connector positioned between the cage and the end cap.

29) US Published Patent Application No. 20050071006—Kirschman discloses a spinal fusion system and method for fusing spinal bones. The '006 Application teaches, "As illustrated in FIG. 11, the housing 32 is generally U-shaped as shown. In the embodiment being described, the housing 32 comprises a well 33 defining multiple sides and comprises a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired." Among other things, it does not appear that the Kirschman invention practices the use of a cage having a trapezoidal divider, an end cap with docking slides and plate including an opening or a connector positioned between the cage and the end cap.

30) US Published Patent Application No. 20050149192—Zucherman discloses an intervertebral body fusion cage with keels and implantation method. The '192 Application teaches, "A wedge-shaped implant 400 with keels 422, 424 implanted from a lateral approach can be used to correct the loss of curvature from a degenerated region of the spine." Among other things, it does not appear that the Zucherman invention practices the use of a cage having a trapezoidal divider, an end cap with docking slides and plate including an opening or a connector positioned between the cage and the end cap.

31) US Published Patent Application No. 20040126407—Falahee discloses intervertebral cage designs. The '407 Application teaches, "[0034] A first preferred embodiment of the invention is depicted in FIG. 1. This design includes an open-faced cage 102, which is constructed of carbon fiber or other radiolucent material but for small dot radiopaque markers (not shown). The device includes a contoured dome-shaped side walls 104, 104' with a flat trapezoidal undersurface. Separate cages and tools may be used for the L5-S1 levels with more pronounced trapezoidal shapes. An indented back wall 110 is used to prevent neurocompression. The side walls preferably include a recessed face with nippled intents 112 and screw holes 114 to receive a locking screw 116. A closing face gate 120 is provided with non-slip nipples and locking screw holes as well." Among other things, it does not appear that the Falahee invention practices the use of a cage having a trapezoidal divider, an end cap with docking slides and plate including an opening or a connector positioned between the cage and the end cap.

32) US Published Patent Application No. 20040204714—Liu, et al. discloses a spinal implant and cutting tool preparation accessory for mounting the implant. The '714 Application discloses, "[0033] In the illustrated embodiment, the longitudinal walls 4 have a substantially trapezoidal contour of which the small base corresponds to the terminal part 5 and the large base corresponds to the terminal part 6. The walls 4 constituting the central part 3c of the implant 1 are so shaped as to transversely project from the terminal bearing parts 5, 6, as can be seen in FIGS. 1 and 6. Thus the walls 4 can penetrate respective openings 19, 21 of the vertebral plates 15, 16 whose edges bear against the bearing surfaces 12, 13 of the flanges 8, 9 (FIG. 6)." Among other things, it does not appear that the Liu invention practices the use of a cage having a trapezoidal divider, an end cap with docking slides and plate including an opening or a connector positioned between the cage and the end cap.

33) U.S. Pat. No. 6,746,484—Liu, et al. enables a spinal implant. The '484 patent discloses, "In the illustrated embodiment, the longitudinal walls 4 have a substantially trapezoidal contour of which the small base corresponds to the terminal part 5 and the large base corresponds to the terminal part 6. The walls 4 constituting the central part 3c of the implant 1 are so shaped as to transversely project from the terminal bearing parts 5, 6, as can be seen in FIGS. 1 and 6. Thus the walls 4 can penetrate respective openings 19, 21 of the vertebral plates 15, 16 whose edges bear against the bearing surfaces 12, 13 of the flanges 8, 9 (FIG. 6)." Among other things, it does not appear that the Liu invention practices the use of a cage having a trapezoidal divider, an end cap with docking slides and plate including an opening or a connector positioned between the cage and the end cap.

34) U.S. Pat. No. 6,712,852—Chung, et al. enables a laminoplasty cage. The '852 patent discloses, "As shown in FIG. 1, the implant 10 is formed from a generally hollow, elongate body having four sides: opposed cephalad and caudal sides 12, 14, and opposed posterior and anterior sides 16, 18 adjacent to the cephalad and caudal sides 12, 14. The implant 10 has a longitudinal axis L and the four sides 12, 14, 16, 18 define an inner lumen 23 (FIG. 2) extending between opposed first and second open ends 22, 24. The sides 12, 14, 16, 18 of the implant 10 can be substantially planar, or can be curved along the longitudinal axis L depending on the intended use. As shown in FIG. 1, the implant 10 is curved along the longitudinal axis L toward the anterior side 18, such that the outer surface of the anterior side 18 has a concave shape." Among other things, it does not appear that the Chung invention practices the use of a cage having a trapezoidal divider, an end cap with docking slides and plate including an opening or a connector positioned between the cage and the end cap.

35) US Published Patent Application No. 20040153155—Chung, et al. discloses a laminoplasty cage. The '155 Application teaches, "[0038] The implant 300 can have a variety of shapes and sizes, and can be substantially planar, curved, or bent. Preferably, the caudal, cephalad, posterior, and anterior sides 314, 314, 316, 318 are substantially planar and form a rectangular or substantially square elongate member." Among other things, it does not appear that the Chung invention practices the use of a cage having a trapezoidal divider, an end cap with docking slides and plate including an opening or a connector positioned between the cage and the end cap.

36) US Published Patent Application No. 20040064184—Chung, et al. discloses a laminoplasty cage. The U.S. Pat. No. 6,712,852—Chung, et al. Patent issued from the '184 Application. The disclosure of the '852 patent and the '184 Application have similar disclosures.

37) U.S. Pat. No. 6,395,035—Bresina, et al. enables a strain regulating fusion cage for spinal fusion surgery. The '035 patent discloses, "FIGS. 5 and 6 show a preferred embodiment of the strain regulation fusion cage 1 according to the invention. The fusion cage 1 has a prism-like exterior shape with a longitudinal axis 2, an upper contact surface 3 and a lower contact surface 4 transverse to its longitudinal axis, and a central cavity 5 for receiving bone graft material that is coaxial to the longitudinal axis 2 and extending between the upper contact surface 3 and the lower contact surface 4. The cross section perpendicular to the longitudinal axis 2 shows an exterior circumference of the fusion cage 1 that has the shape of an irregular polygon. The lower contact surface 4 is even and extends transversely to the longitudinal axis 2." Among other things, it does not appear that the Bresina invention practices the use of a cage having a trapezoidal divider, an end cap with docking slides and plate including an opening or a connector positioned between the cage and the end cap.

38) U.S. Pat. No. 6,997,953—Chung, et al. enables a method of implanting a laminoplasty. The U.S. Pat. No. 6,997,953—Chung, et al. Patent issued from US Published Patent Application No. 20040153155—Chung, et al. The disclosure of the '953 patent and the '155 Application have similar disclosures.

39) U.S. Pat. No. 6,712,825—Aebi, et al. enables a spinal space distractor. Among other things, it does not appear that the Aebi invention practices the use of a cage having a trapezoidal divider, an end cap with docking slides and plate including an opening or a connector positioned between the cage and the end cap.

40) US Published Patent Application No. 20040225360—Malone discloses a laminoplasty cage. The '360 Application teaches, "A cage body 22 is provided having a posterior end 24 and an anterior end 26 and defining an internal cavity 28 and a longitudinal axis 30. The cage body 22 is typically between 20-25 mm in length and may be of a variety of diameters, dimensions and heights. The cage body 22 has an outer surface 32 and a plurality of radial apertures 34 or pathways extending through the outer surface 32 in communication with the internal cavity 28 in a preselected pattern. Preferably, there is a first non-perforated zone 36 extending from the posterior end 24 of the cage body 22 a preselected length, preferably 5-10 mm, toward its anterior end 26, second and third non-perforated zones 38, 40 on the lateral sides of the cage body 22 extending in opposing relation from the first zone 36 further toward the anterior end 26, and two opposed perforated zones 42, 44 oriented cephalad (or to the superior side) and caudad (or to the inferior side) so that upon insertion of the device the perforated zones 42, 44 will be adjacent the vertebral bodies to be fused to allow bone growth across the vertebral interspace." Among other things, it does not appear that the Malone invention practices the use of a cage having a trapezoidal divider, an end cap with docking slides and plate including an opening or a connector positioned between the cage and the end cap.

41) U.S. Pat. No. 7,166,110—Yundt enables a method, system and apparatus for interbody fusion. The '110 patent discloses, "As shown in FIG. 8, material restrictor 70 may include a shell 100 that defines a central cavity 102. Shell 100 may have a top surface 104 and a bottom surface 106 as well as ends 108, 110. In some embodiments, one end 110 of material restrictor 70 may be substantially closed and the other end 108 may be at least partially open (e.g. opening 152)." Among other things, it does not appear that the Yundt invention practices the use of a cage having a trapezoidal divider, an end cap with docking slides and plate including an opening or a connector positioned between the cage and the end cap.

42) U.S. Pat. No. 6,863,673—Gerbec, et al. enables methods for adjustable bone fusion implants. The '673 patent discloses, "As depicted in FIG. 2, fusion implant 10 comprises a housing 11 and a reinforcing member 16. Housing 11 comprises a cap 12 that is selectively connected to a base 14. Cap 12 comprises a cap plate 18 having an interior face 20 and an opposing exterior face 22 that each extend between a proximal end 24 and an opposing distal end 26. The term "plate" as used in the specification and appended claims is broadly intended to include not only structures that have a flat or substantially flat surface but also, for example, members that are curved, sloped, have regular or irregular formations thereon, and that may or may not have openings extending therethrough." Among other things, it does not appear that the Gerbec invention practices the use of a cage having a trapezoidal divider, an end cap with docking slides and plate including an opening or a connector positioned between the cage and the end cap.

43) U.S. Pat. 7,182,782—Kirschman enables methods for adjustable bone fusion implants. The '782 patent discloses, "As illustrated in FIG. 11, the housing 32 is generally U-shaped as shown. In the embodiment being described, the housing 32 comprises a well 33 defining multiple sides and comprises a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired." Among other things, it does not appear that the Kirschman invention practices the use of a cage having a trapezoidal divider, an end cap with docking slides and plate including an opening or a connector positioned between the cage and the end cap.

44) US Published Patent Application 20070129805—Braddock Jr., et al. teaches an end device for a vertebral implant. The '805 Application discloses, "FIGS. 2 and 3 illustrate the end device 10 with FIG. 2 illustrating an open orientation and FIG. 3 a closed orientation. An end device 10 is connected to the implant 100 and prevents subsidence, expulsion, and/or enables fusion. An implant 100 may be equipped with a single or multiple end devices 10. For implants 100 equipped with multiple end devices 10, the devices may be the same or different. In the embodiments of FIGS. 2 and 3, end device 10 includes a base 20, opening 30, and a gate 40. Base 20 includes a bottom 21 and a sidewall 22. A receiving area 26 is framed by the base 20 and gate 40 to receive the implant 100.

A spacing device 101 may be positioned on a second side 12 of the end device 10. The spacing device 101 may have an angled shape such that the end device 10 with implant 100 corresponds to the curvature of the spine. The spacing device 101 may be separately attached to the bottom surface, or may be integral with the bottom surface.

FIG. 9 illustrates one embodiment of the spacing device 101 with a first side 102 and an opposing second side 103. Apertures 104 are spaced about the device 101 and are sized to receive the spikes 27 that extend outward from the end device 10 to connect the spacing device 101 to the end device 10. Spikes 105 extend outward from the second side 103 to bite into the vertebral member and prevent movement or expulsion of the device 101." Among other things, it does not appear that the Braddock invention practices the use of a cage having a trapezoidal divider, an end cap with docking slides and plate including an opening or a connector positioned between the cage and the end cap.

45) U.S. Pat. No. 5,558,674—Heggeness, et al. enables devices and methods for posterior spinal fixation. Among other things, it does not appear that the Heggeness invention practices the use of a cage having a trapezoidal divider, an end cap with docking slides and plate including an opening or a connector positioned between the cage and the end cap.

46) U.S. Pat. No. 7,232,463—Falahee enables intervertebral cage designs. The '463 patent discloses, "This design includes an open-faced cage 102, which is constructed of carbon fiber or other radiolucent material but for small dot radiopaque markers (not shown). The device includes a contoured dome-shaped side walls 104, 104' with a flat trapezoidal undersurface. Separate cages and tools may be used for the L5-S1 levels with more pronounced trapezoidal shapes." Among other things, it does not appear that the Falahee invention practices the use of a cage having a trapezoidal divider, an end cap with docking slides and plate including an opening or a connector positioned between the cage and the end cap.

47) U.S. Pat. No. 6,926,737—Jackson, et al. enables a spinal fusion apparatus and method. The '737 patent discloses, "The fusion enhancing apparatus 1 includes a pair of bone receiving cages or implants 10 and 11 that are joined to a connecting plate 12 that joins a pair of end caps 15 and 16 by a pair of set screws 13 and 14 respectively." Among other things, it does not appear that the Jackson invention practices the use of a cage having a trapezoidal divider, an end cap with docking slides and plate including an opening or a connector positioned between the cage and the end cap.

48) U.S. Pat. No. 6,776,798—Camino, et al. enables a spacer assembly for use in spinal surgeries having end cap which includes serrated surface. The '798 patent discloses, "As shown in FIG. 2, end cap 10 is coupled to either end 24, 26 of spacer 12 for use in interbody fusion surgeries. End cap 10, remains at either end 24, 26 of spacer 12 without slipping down within passageway 32. As shown in FIGS. 2-5, end cap 10 is formed to include an outer end 50, an inner end 52, and a tapered side wall 54 converging from outer end 50 toward inner end 52. Referring now to FIG. 4, side wall 54 includes a generally cylindrical inner surface 56 having a constant diameter 58 and defining a passageway 60 and an outer surface 62. While end cap 10 is shown in FIGS. 4 and 5 with generally circular outer and inner ends 50, 52, it is appreciated that outer and inner ends 50, 52 may be formed in a variety of shapes to cooperate with a variety of opposite ends 24, 26 of spacers 12 and may be positioned to lie generally parallel to one another or angled relative to one another. It is also appreciated that end caps 10 may vary in size to cooperate with a variety of spacers 12." Among other things, it does not appear that the Camino invention practices the use of a cage having a trapezoidal divider, an end cap with docking slides and plate including an opening or a connector positioned between the cage and the end cap.

49) US Published Patent Application 20080021476—Kirschman teaches a spinal fusion system utilizing an implant plate having at least one integral lock and ratchet lock. The '476 Application discloses, "As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel area 52, the sides 42a and 42b become associated with the sides 48a and 50a. It should be understood that the cover 42 is not directed permanently secured to the housing 32 after it is received in channel area 52. This feature permits the housing 32 secured to the housing 32 to migrate or float relative to the cover 42 even after the cover 42 is fixed to one or more of the spinal bones 10-16 as illustrated in FIGS. 6 and 20." Among other things, it does not appear that the Kirschman invention practices the use of a cage having a trapezoidal divider, an end cap with docking slides and plate including an opening or a connector positioned between the cage and the end cap.

50) US Published Patent Application 20080015694—Tribus teaches a spine reduction and stabilization device. The '694 Application discloses, "FIG. 1C illustrates an intervertebral body 100 mounted to a second plate 102. This embodiment is similar to the embodiment depicted in FIGS. 1A and 1B with various modifications. The intervertebral body 100 includes legs 104 and 106 with channels 108 and 109 in a superior surface 107 of the legs 104 and 106. In an exemplary embodiment, the legs 104 and 106 can also include channels (not shown) in an inferior surface 113 of the legs 104 and 106. The second plate 102 includes interference holes 111, reduction slots 115 and 116, and through holes 118. The second plate 102 also includes an opening 120 with two receiving slots 122 such that a locking plate 150, as illustrated with reference to FIGS. 3A and 3B, can be mounted to the second plate 102. The receiving slots 122 can be tapered surfaces capable of receiving one or more mounting protrusions 152 of the locking plate 150. Alternatively, there can be any number of receiving slots, and the receiving slots can be of any shape and/or configuration such that the locking plate 150 can be securely mounted to the second plate 102. Similarly, in alternative embodiments, the locking plate can include any number, shape, and/or configuration of mounting protrusions." Among other things, it does not appear that the Tribus invention practices the use of a cage having a trapezoidal divider, an end cap with docking slides and plate including an opening or a connector positioned between the cage and the end cap.

51) US Published Patent Application 20070255413—Edie, et al. teaches expandable intervertebral spacers and methods of use. The '413 Application discloses, "FIGS. 3-5 illustrates one exemplary embodiment of the intervertebral spacer 10. The intervertebral spacer 10 comprises an inferior member 12 and a superior member 60 movable with respect to the inferior member 12 from a retracted position to an extended position. As will be described in more detail below, the inferior member 12 includes a first cylinder 22, and the superior member 60 includes a second cylinder 72 that is insertable into the first cylinder 22. The cylinders 22 and 72 together define a expansion chamber. When fluid is introduced into the expansion chamber, the superior member 60 is urged away from the inferior member 12. While cylinders 22 and 72 are shown having a circular cross-section, those skilled in the art will appreciate that the cylinders 22 and 72 can have other shapes, such as square, rectangular, oval, kidney-shape, etc." Among other things, it does not appear that the Edie invention practices the use of a cage having a trapezoidal divider, an end cap with docking slides and plate including an opening or a connector positioned between the cage and the end cap.

52) U.S. Pat. No. 6,808,538—Papponeau enables a vertebral body spacer having variable wedged endplates. The '538 patent reads, "Referring to FIG. 2, in certain preferred embodiments, main body 22 has a longitudinal axis designated A-A. Main body 22 is preferably substantially cylindrical in shape and has an exterior surface that is coaxial with longitudinal axis A-A. In other preferred embodiments, main body 22 may be polygon-shaped in cross section. Main body 22 may have any geometric shape, such as the shape of an oval or ellipse. Main body 22 preferably has an upper end 28 with a first substantially concave-shaped socket 30 formed therein. The upper end 28 includes an upper edge 32 that surrounds the first concave socket 30. The upper edge 32 includes a first plane 34 and a second plane 36 that are angled relative to one another. The planes 34, 36 intersect at respective apexes 38 A and 38 B. Upper edge 32 also includes opposing first and second retaining clips 40 A and 40 B. First retaining clip 40 A has an inwardly extending portion 42 A and second retaining clip 40 B has an inwardly extending projection 42 B. As will be described in more detail below, the retaining clips 40 A, 40 B are designed to pass through retainer clip openings that extend through the endplates shown in FIG. 1 for securing the endplates to the respective upper and lower ends of main body 22." Among other things, it does not appear that the Papponeau invention practices the use of a cage having a trapezoidal divider, an end cap with docking slides and plate including an opening or a connector positioned between the cage and the end cap.

53) U.S. Design Pat. No. D524,942—Felix shows and claims a surgical implant. Among other things, it does not appear that the Felix invention practices the use of a cage having a trapezoidal divider, an end cap with docking slides and plate including an opening or a connector positioned between the cage and the end cap.

54) U.S. Pat. No. 5,192,327—Brantigan enables a surgical prosthetic implant for vertebra. The '327 patent discloses, "The device 10 is an oval ring plug 11 generally shaped and sized to conform with the disc space between adjoining vertebrae in a vertebral column. The plug 11 has opposed sides 11a and ends 11b, flat, ridged top and bottom faces 11c and a central upstanding aperture 11d therethrough. The ends 11b have relatively wide and long horizontal peripheral slots 11e therethrough preferably extending into the sides 11a and communicating with the central aperture 11d." Among other things, it does not appear that the Brantigan invention practices the use of a cage having a trapezoidal divider, an end cap with docking slides and plate including an opening or a connector positioned between the cage and the end cap.

55) U.S. Pat. No. 6,395,030—Songer, et al. enables a spinal fixation system. The '030 patent discloses, "Referring to FIGS. 1-3, an implantable spinal vertebral replacement device is shown. Specifically, device 10 comprises a tubular cage 12 of oval cross section and made for example of titanium or a carbon fiber composite. Alternatively, cage 12 may be made of a length of hollow bone typically having noncircular ends, cut to fit, and having a lumen that extends from end to end of the bone." Among other things, it does not appear that the Songer invention practices the use of a cage having a trapezoidal divider, an end cap with docking slides and plate including an opening or a connector positioned between the cage and the end cap.

56) U.S. Pat. No. 6,409,766—Brett enables a collapsible and expandable interbody fusion device. The '766 patent reads, "A fusion cage 10 of the present invention includes an upper body 12 connected to a lower body 14 by side articulated supports 16, 18. The fusion cage 10 expands and contracts between a fully open or expanded position (FIGS. 1 and 2), through a midway, partially collapsed position (FIGS. 3 and 4), to a fully closed or collapsed position (FIGS. 5 and 6)." Among other things, it does not appear that the Brett invention practices the use of a cage having a trapezoidal divider, an end cap with docking slides and plate including an opening or a connector positioned between the cage and the end cap.

57) US Published Patent Application 20040073314—White, et al. teaches vertebral body and disc space devices. The '314 Application discloses, "[0055] In FIGS. 1-2, a vertebral replacement device 10 includes a connecting member 12, an upper member 30, and a lower member 40. Device 10 is illustrated as having a tubular form that extends along a longitudinal axis 11 and defines a chamber extending therethrough along axis 11. Bone growth can occur through this chamber for fusion between the vertebral bodies supported at each end of device 10." Among other things, it does not appear that the White invention practices the use of a cage having a trapezoidal divider, an end cap with docking slides and plate including an opening or a connector positioned between the cage and the end cap.

58) U.S. Pat. No. 6,761,738—Boyd enables a reinforced molded implant formed of cortical bone. The '738 patent reads, "FIG. 11 is a perspective illustration of another embodiment of a lordotic implant assembly according to the present invention. Implant assembly 190 defines a longitudinal axis 191 and includes a first strut 192, a second strut 194 and a third strut 196. Each of the respective struts 192, 194 and 196 include pairs of opposite bone-engaging portions 210 and 212, 214 and 216, and 218 and 220, respectively." Among other things, it does not appear that the Boyd invention practices the use of a cage having a trapezoidal divider, an end cap with docking slides and plate including an opening or a connector positioned between the cage and the end cap.

59) US Published Patent Application 20050071008—Kirschman teaches a spinal fusion system and method for fusion spinal bones. The '008 Application discloses, "As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel area 52, the sides 42a and 42b become associated with the sides 48a and 50a. It should be understood that the cover 42 is not directed permanently secured to the housing 32 after it is received in channel area 52. This feature permits the housing 32 secured to the housing 32 to migrate or float relative to the cover 42 even after the cover 42 is fixed to one or more of the spinal bones 10-16 as illustrated in FIGS. 6 and 20." Among other things, it does not appear that the Kirschman invention practices the use of a cage having a trapezoidal divider, an end cap with docking slides and plate including an opening or a connector positioned between the cage and the end cap.

60) US Published Patent Application 20060287725—Miller teaches a lateral expandable interbody fusion cage. The '725 Application discloses, "The laterally expandable interbody fusion cage of the present invention comprises an outer cage 12 and an inner cage 14 that can be inserted sideways into the outer cage 12. The inner cage 14 has a notch 16 for an expander to grip on the front of the inner cage 14. The inner cage 14 can be filled with graft material prior to insertion." Among other things, it does not appear that the Miller invention practices the use of a cage having a trapezoidal divider, an end cap with docking slides and plate including an opening or a connector positioned between the cage and the end cap.

61) US Published Patent Application 20100004752—White, et al. teaches vertebral body and disc space replacement devices. The '752 Application discloses, "Referring now to FIGS. 22-23, there is shown another embodiment vertebral replacement device 500. Vertebral replacement device 500 includes one or more upper or lower end or disc replacement members 600, 601 and one or more connecting or vertebral body members 510 engaged to disc replacement members 600, 601. Vertebral replacement device 500 has application in corpectomy procedures in which one or more vertebrae are removed. Applications in disc space replacement and interbody fusion procedures are also contemplated. In the illustrated embodiment, vertebral replacement device 500 includes three members stacked one upon the other. Other embodiments contemplate two member stacks, or stacks comprising four or more members." Among other things, it does not appear that the White invention practices the use of a cage having a trapezoidal divider, an end cap with docking slides and plate including an opening or a connector positioned between the cage and the end cap.

62) U.S. Pat. No. 6,942,697—Lange, et al. enables a pair of lumbar interbody implants and method of fusing together adjoining vertebrae bodies. The '697 patent reads, "In FIG. 1 the reference number 3 refers to a first implant 1 and a second implant 2. The first implant 1 and the second implant 2 are in the form of a cage as shown in FIGS. 3 and 7. The implants 1 and 2 have a hollow space 28 which is filled with bone graft material, not shown, that will grow out and into the bone tissue of the adjoining vertebrae 4. The implants 1 and 2 are preferably made of radiolucent carbon fiber reinforced polymers or of another rigid biologically acceptable and preferably radiolucent material." Among other things, it does not appear that the Lange invention practices the use of a cage having a trapezoidal divider, an end cap with docking slides and plate including an opening or a connector positioned between the cage and the end cap.

63) U.S. Pat. No. 6,582,432—Michelson enables a cap for use with artificial spinal fusion implant. The '432 patent reads, "The open end 54 of the cylindrical implant 50 has an internal thread 51 for receiving a complementary cap 52 which has an external thread 58 for engaging the internal threads 51 of the cylindrical member 50. As shown in FIG. 5, cap 52 has an exposed exterior surface opposite an unexposed interior surface with a mid-longitudinal axis passing through the exterior and interior surface of the cap. A cross section of cap 52 along a plane parallel to the mid-longitudinal axis is at least in part convex along the exterior surface of cap 52. A second cross-section of cap 52 along a second plane parallel to the mid-longitudinal axis of cap 52 is curved along at least a portion of the exterior surface of cap 52 so that the curvature of the first and second cross-sections form a portion of a sphere. As shown in FIG. 4a, cap 52 has rounded edges in a plane transverse the mid-longitudinal axis of cap 52. The cap 52 has a hexagonal opening 59 for use with an alien wrench for tightening the cap." Among other things, it does not appear that the Michelson invention practices the use of a cage having a trapezoidal divider, an end cap with docking slides and plate including an opening or a connector positioned between the cage and the end cap.

64) U.S. Pat. No. 5,980,522—Koros, et al. enables expandable spinal implants. The '522 patent reads, "The removable cap means, illustrated as a circular cap 140, is threadably secured to the open end 108 of the housing 102. The cap has an outer slightly dome-shaped face 141 and a smaller thin concentric cylinder section 142 extending from the underside of the cap 140. The diameter of the cap 140 is the same as the diameter of the outer wall 104 of the cylinder-shaped housing 102. The ring-shaped rim on the underside of the cap 140 has the same dimensions as the face 109 of the housing so that when the cap 140 is screwed onto the end of the housing 102, the rim of the cap 140 lies flush against the face 111 of the housing and forms a sealed end for the housing without any overhang. The face 109 of the housing has eight notches 115 cut therein. The notches will prevent the cap 140 from unscrewing long after the surgery." Among other things, it does not appear that the Koros invention practices the use of a cage having a trapezoidal divider, an end cap with docking slides and plate including an opening or a connector positioned between the cage and the end cap.

65) U.S. Pat. No. 5,968,098—Winslow enables an apparatus for fusing bone structures. The '098 patent reads, "With reference now to FIG. 5 and FIG. 7B, the trailing end portion 122 of implant body 102 has a generally annular recess 124 which receives end cap 104. An internal thread 126 is disposed adjacent annular recess 124 and cooperates with external thread 128 on the periphery of end cap 104 to mount the end cap to implant body 102. Trailing end portion 122 also includes a pair of diametrically opposed notches 130. Notches 130 are dimensioned to be engaged by corresponding structure of an insertion apparatus utilized in inserting the implant within the vertebral column. End cap 104 includes a central threaded aperture 132 which threadably engages corresponding structure of the insertion apparatus to assist in the mounting of the cap 104 on implant body 102." Among other things, it does not appear that the Winslow invention practices the use of a cage having a trapezoidal divider, an end cap with docking slides and plate including an opening or a connector positioned between the cage and the end cap.

66) U.S. Pat. No. 5,458,638—Kuslich, et al. enables a non-threaded spinal implant. The '638 patent reads, "When the implant 10 is in place in an intervertebral space, circular axial opening 40 and hexagon axial opening 46 are covered by caps 18 and 20. Shown best in FIGS. 8 and 9, the leading end cap 18 includes a cylindrical hub portion 50 and an annular flange 52 extending from hub portion 50. Also extending from hub portion 50 on the side opposite flange 52 is a tapered cap portion 54 which extends from a large diameter 55 and tapers inwardly to a smaller diameter terminal end 56. An angle of taper $A_5$ (FIG. 8) is preferably about 15° to correspond with the angle of taper $A_1$ (FIG. 2) of body 12. The large diameter 55 is preferably selected to equal the diameter of body 12 at leading end 14. Flange 52 is selected to be snap received into annular groove 42. So received, cap 18 is permanently attached to the leading end 14 covering axial opening 40." Among other things, it does not appear that the Kuslich invention practices the use of a cage having a trapezoidal divider, an end cap with docking slides and plate including an opening or a connector positioned between the cage and the end cap.

SUMMARY OF THE INVENTION

Unlike traditional spinal implants, the present invention provides a biocompatible cage that assists the surgical team in not impinging the spinal cord with the implant. Post operative and prior to complete arthrodesis, the generally wedge-like implant inhibits extrusion of the cage against the spinal cord. Utilization of an end cap with the biocompatible implant supplements stabilization of the biocompatible implant. And inclusion of a connector positioned between the biocompatible implant and the end cap allows the spinal column to be distracted to a greater distance than the length of the biocompatible implant.

An aspect of the present invention is to provide a biocompatible cage.

Still another aspect of the present invention is to provide a generally wedge-like cage.

It is still another aspect of the present invention to provide an implant having select embodiments that can be implanted through the patient's frontal or rearward side.

Yet still another aspect of the present invention is to provide a cage that can be severed across a first cross-section or severed across a first cross-section and a second cross-section to create a custom fitted implant for the surgically created cavity.

Still another aspect of the present invention is to provide a biocompatible cage including brakes.

Yet another aspect of the present invention is to provide an end cap attachable to vertebra for assisting with the stabilization of the spinal implant.

It is still another aspect of the present invention to provide a connector capable of extending the length of the spinal implant.

Still another aspect of the present invention is to provide a spinal implant capable of enhancing lordosis.

Yet another aspect of the present invention is to provide a biocompatible implant and end cap combination.

It is still another aspect of the present invention to provide a biocompatible, end cap and connector combination.

A preferred embodiment of the current invention can be described as a combination capable of insertion about a surgically created cavity proximate to one or more vertebrae; the combination comprising: a) a biocompatible cage comprising:
i) a length having a longitudinal axis; ii) a first end perimeter creating a trapezoidal aperture at a first end of the biocompatible cage; and iii) a plurality of spikes extending outwardly from the first end perimeter in a lengthwise direction parallel the longitudinal axis; b) an end cap comprising: i) a border comprising a plurality of bores capable of aligning with some or all of the plurality of spikes; ii) a plate extending in the lengthwise direction away from the biocompatible cage and comprising at least one opening for receiving a fastener; and iii) a pair of opposed docking slides extending from the border in the lengthwise direction toward the biocompatible cage; and c) a connector, capable of receiving the docking slides, positioned between the biocompatible cage and the end cap; the connector comprising: i) a first leg comprising: A) a plurality of apertures capable of aligning with some of the plurality of spikes; and B) a plurality of pins capable of aligning with some of the plurality of bores; ii) a second leg comprising: A) a plurality of apertures capable of aligning with some of the plurality of spikes; and B) a plurality of pins capable of aligning with some of the plurality of bores; and iii) an anterior section joining a first end of the first leg and a first end of the second leg, wherein the anterior section shares a margin facing the biocompatible cage with the legs and comprises an opposing margin extending further away from the biocompatible cage than the pluralities of pins, and wherein the anterior section is anterior to the plate.

Another preferred embodiment of the current invention can be described as a combination capable of insertion about a surgically created cavity proximate to one or more vertebrae; the combination comprising: a) a biocompatible cage comprising: i) a length having a longitudinal axis; ii) a first end perimeter creating a trapezoidal aperture at a first end of the biocompatible cage; and b) an end cap comprising: i) a border comprising four sides; and ii) a plate extending in the lengthwise direction parallel the longitudinal axis away from the biocompatible cage and comprising at least one opening for receiving a fastener; and iii) a pair of opposed docking slides extending from the border in the lengthwise direction toward the biocompatible cage and capable of docking with the first end perimeter of the biocompatible cage.

Still another preferred embodiment of the current invention can be described as a combination capable of insertion about a surgically created cavity proximate to one or more vertebrae; the combination comprising: a) a biocompatible cage comprising: i) a length having a longitudinal axis; ii) a first end perimeter creating an aperture at a first end of the biocompatible cage; and b) an end cap comprising: i) a border; and ii) a plate extending in the lengthwise direction parallel the longitudinal axis away from the biocompatible cage and comprising at least one opening for receiving a fastener; and iii) opposed docking slides extending from the border in the lengthwise direction toward the biocompatible cage and capable of docking with the first end perimeter of the biocompatible cage.

Yet another preferred embodiment of the current invention can be described as a combination capable of insertion about a surgically created cavity proximate to one or more vertebrae; the combination comprising: a) a biocompatible cage comprising: i) a length having a longitudinal axis; ii) a first end perimeter creating an aperture at a first end of the biocompatible cage; and iii) a plurality of spikes extending outwardly from the first end perimeter in a lengthwise direction parallel the longitudinal axis; and b) an extension for the biocompatible cage extending in the lengthwise direction away from the biocompatible cage; the extension comprising: i) a first leg comprising: A) a first side comprising a plurality of apertures capable of aligning with some of the plurality of spikes; and B) a second side opposite the first side comprising a plurality of pins extending in the lengthwise direction away from the biocompatible cage; and ii) a second leg comprising: A) a first side comprising a plurality of apertures capable of aligning with some of the first plurality of spikes; and B) a second side opposite the first side comprising a plurality of pins extending in the lengthwise direction away from the biocompatible cage.

Still another preferred embodiment of the current invention can be described as an end cap for a biocompatible spinal implant; the end cap comprising: a) a border capable of abutting a longitudinally positioned outermost brace of the biocompatible implant, wherein the outermost brace comprises an aperture; b) a plate comprising at least one opening for receiving a fastener; the plate positioned about an edge of the border and extending outward from the biocompatible spinal implant in a lengthwise direction parallel a longitudinal axis of the biocompatible implant; and c) a pair of opposed docking slides extending from the border in the lengthwise direction toward the biocompatible cage for engaging inward sides of the longitudinally positioned outermost brace.

Yet still another preferred embodiment of the current invention can be described as a connector capable of being positioned between a biocompatible spinal implant and another spinal hardware distal from the biocompatible spinal implant; the connector comprising: a) a first leg comprising: i) a plurality of pins positioned on a first side, wherein the pins extend away from the biocompatible spinal implant in a lengthwise direction parallel a longitudinal axis of the spinal implant; ii) a second side opposite the first side comprising a plurality of apertures capable of aligning with some of a plurality of spikes extending from the biocompatible spinal implant in the lengthwise direction; b) a second leg comprising: i) a plurality of pins positioned on a first side, wherein the pins extend away from the biocompatible spinal implant in the lengthwise direction; ii) a second side opposite the first side comprising a plurality of apertures capable of aligning with some of the plurality of spikes extending from the biocompatible spinal implant in the lengthwise direction; and c) an anterior section joining a first end of the first leg and a first end of the second leg.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is a cage or implant that can be inserted into a cavity of the spinal column. Surgical removal of mammalian spinal tissue in one or more spinal regions creates the cavity or cavities that will receive the implant or implants. It has been discovered that many embodiments of the current implant can be useful for spine surgeries and can assist in stabilizing injured, deformed and or degenerative spines. Preferred embodiments of the current invention can be employed with thoracic or lumbar spinal procedures. Still other preferred embodiments of the present invention are particularly suited for corpectomy or partial corpectomy procedures.

After insertion of the implant into the cavity, the biocompatible cage and the end cap or the end cap and connector combinations assist in stabilizing the spinal column against rotational movement and the combinations also resist the compression forces associated with gravity on the spinal column. It has been discovered that the biocompatible cage, end cap and connector combination is particularly useful for assisting in the restoration of normal anatomical height and angulation of an abnormal vertebral body. Select preferred embodiments of the present invention can be implanted through the patient's anterior or ventral side. The current spinal implants are custom fitted for the surgical cavity into which they will be inserted, i.e., the cage can be manufactured to fit the surgical cavity or the cage can be severed across a first cross section or the cage can be severed across first and second cross sections to size the cage to fit the cavity.

Preferred embodiments of the current biocompatible cage are generally trapezoidal in shape and are manufactured of titanium alloys, stainless steel, resorbable polymers, non-resorbable polymers or any other composition acceptable in the art. However, it has been discovered that end caps and/or connectors of the present invention can be manufactured to be compatible with cages of generally square or rectangular dimensions.

Within the scope of the present invention, it has advantageously been discovered that the trapezoidal cages can have a width of from about six to about fifteen millimeters, as measured along the narrowest parallel of the trapezoid, and a depth of from about eight millimeters to about fifteen millimeters, as measured along a converging side of the trapezoid. Generally the spacing between dividers of the cage is from about five to about ten millimeters, as measured from outward side to outward side of the series of dividers. Openings of the cages of the current invention into which bone graft, osteogenic and/or arthrodesis accelerating substances are packed can have areas from about 36 millimeters$^2$ to 225 millimeters$^2$ or greater. Custom made biocompatible cages having lengths that range from about twelve millimeters to about seventy millimeters.

Preferred embodiments of the end caps of the present invention have dimensions that are compatible with biocompatible cage. In select preferred embodiments, the slides can extend away from the body of the end cap for distances of from about two millimeters to about ten millimeters. Some preferred embodiments of the end caps are provided with bores capable of engaging spikes that extend away from the biocompatible cage.

Preferred embodiments of the connectors of the current invention have legs with heights of about two millimeters and pins that extend about one and one-half millimeters beyond the legs. Anterior widths of the connectors range from about six millimeters to about fifteen millimeters. The anterior heights of the connectors are about seven millimeters. And depths of the connectors range from about six millimeters to more than fifteen millimeters.

Meeting a long felt but unfilled need in the spinal surgical arts, the unique structures of the present combinations allow the surgical team to, among other things, enhance the length of the spinal column from about two millimeters to about twenty millimeters more than the span of the biocompatible cage, when the patient's medical condition requires. Contact between the surgical cavity wall and the wedge-like cage can also inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by the cage enhances local areas of arthrodesis between the vertebra and the bone graft. Select preferred embodiments of the present invention are provided with lateral brakes to further impede the implant from contacting the spinal column.

Figure 1:
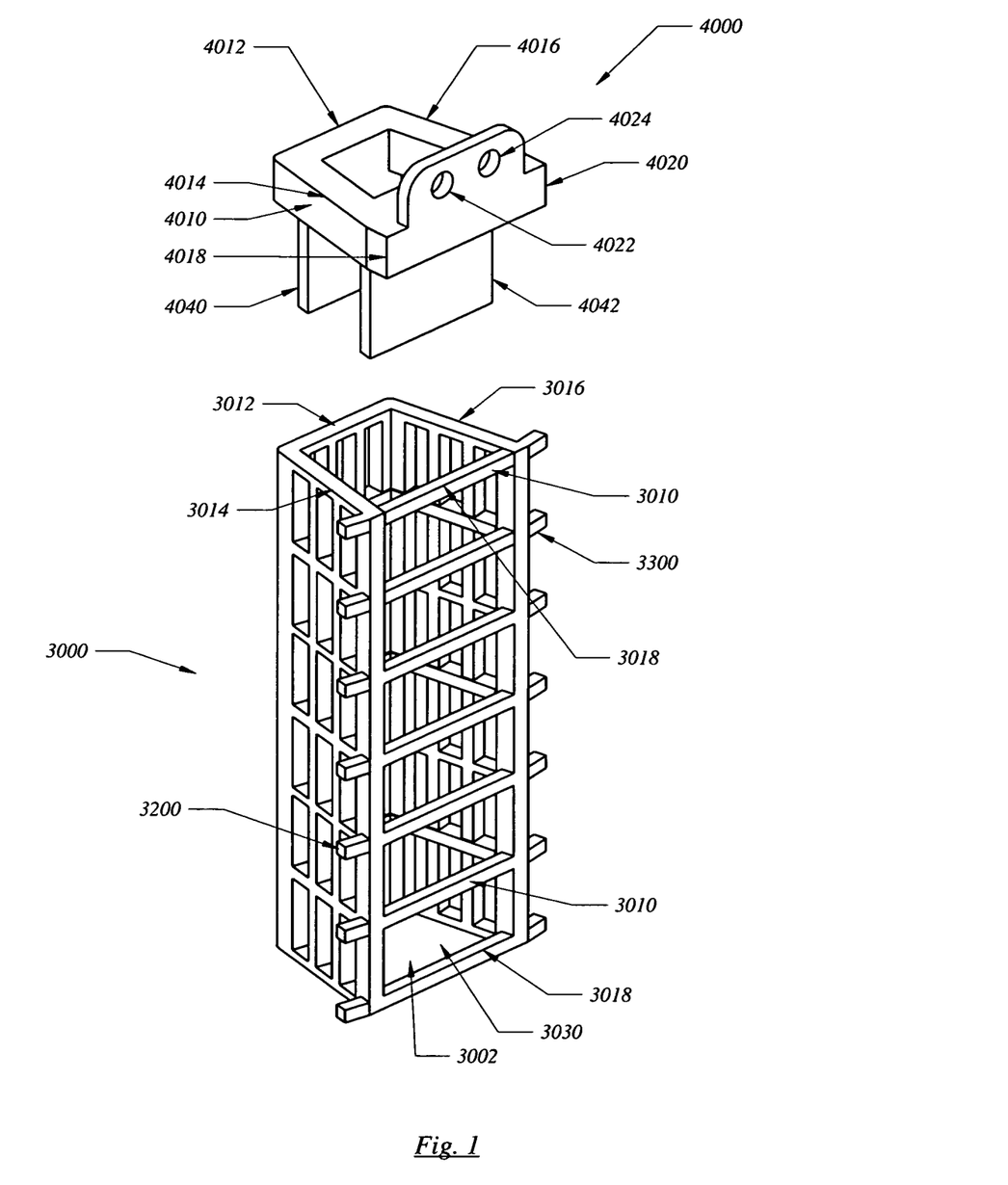
FIG. 1 is an exploded perspective of a preferred embodiment enabling a biocompatible implant and end cap combination.

FIG. 1 is an exploded perspective enabling a biocompatible cage (3000) and end cap (4000) combination. Biocompatible cage (3000) has a series of trapezoidal dividers or braces (3010) and a plurality of receptacles (3002) that can be packed with osteogenic materials, arthrodesis accelerating substances or other substances prior to the completion of spinal surgery. Implant (3000) is manufactured of titanium, stainless steel, resorbable polymers, non-resorbable polymers or combinations thereof. By way of illustration, dividers or braces (3010) have inward sides (3012) (after insertion into the surgically created cavity, positioned near the dura mater of the spinal cord), outward side (3018) (proximate the surgeon after insertion into the surgically created cavity), first converging or lateral side (3014) and second converging or lateral side (3016). The combination of each inward side (3012), outward side (3018), first converging side (3014) and second converging side (3016) creates trapezoidal aperture (3030). Select preferred embodiments of biocompatible cage (3000) can be provided with one or more lateral brakes (3200, 3300).

A preferred embodiment of end cap (4000) is provided with implant facing border or boundary (4010) proximate implant (3000) and plate (4020) that, after insertion into the patient, is distal from biocompatible cage (3000), but proximate to the surgical team. In select preferred embodiments, border (4010) and plate (4020) are integral. Plate (4020) is provided with openings (4022, 4024) for receiving fasteners (not shown in this view). The fasteners, such as screws, are capable of securely attaching plate (4020) to bone. When the combination of implant (3000) and end cap (4000) are assembled as a unit, plate (4020) extends outward and away from border or boundary (4010) in a longitudinal direction parallel the lengthwise axis of biocompatible cage (3000). Boundary (4010) includes shortest side (4012), longest side (4018), first converging side (4014) and second converging side (4016). Extending from border (4010) toward cage (3000) are parallel docking slides (4040, 4042) for engaging inward side (3012) and outward side (3018) of outermost brace (3010) of implant (3000). As shown in FIG. 1, border (4010) is a four-side trapezoidal configuration; however, within the scope of the present invention, when engineering parameters require, other borders (4010) can be squared or rectangular.

Figure 2:
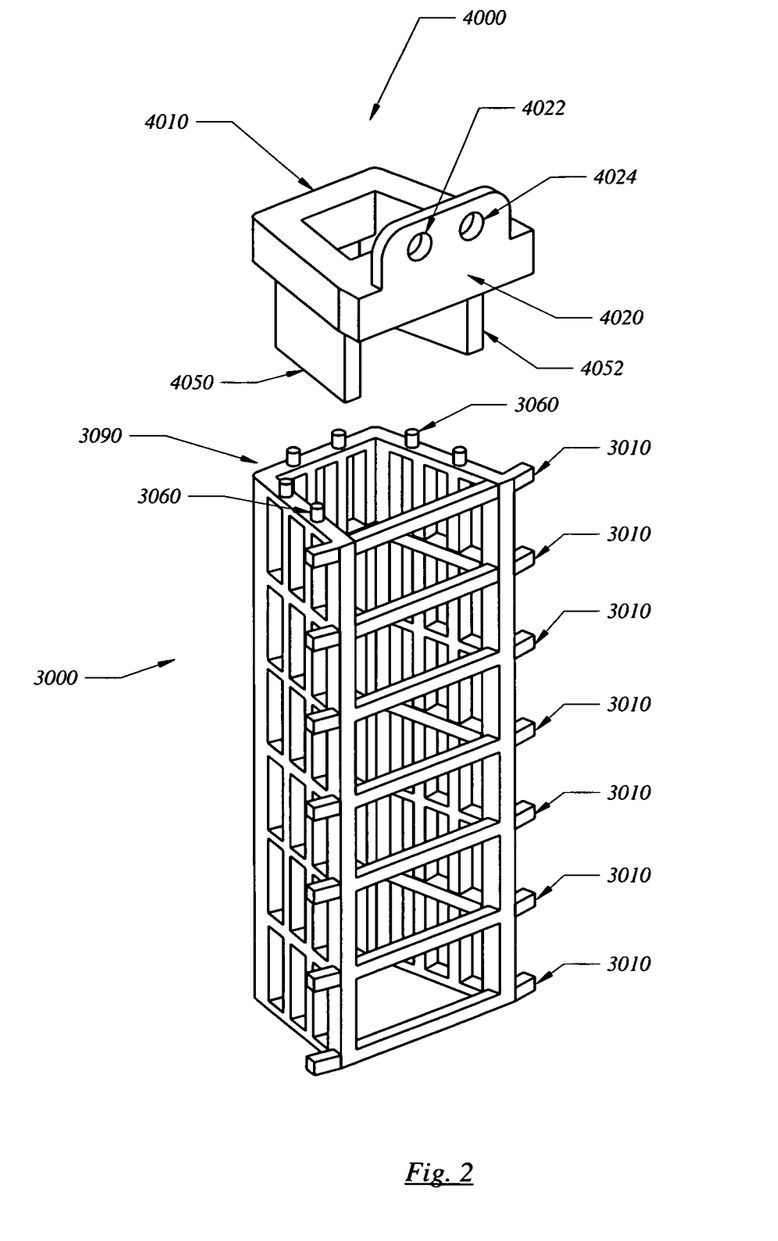
FIG. 2 is an exploded perspective of another preferred embodiment enabling a biocompatible implant and end cap combination.

With reference to FIG. 2, another preferred embodiment of biocompatible cage (3000) that utilizes spikes (3060) is enabled. Except for spikes (3060) and the docking slides (4050 and 4052), the structural elements for the FIG. 2 implant (3000) are identical to the structures enabled by FIG. 1. As shown in FIG. 2, docking slides (4050 and 4052) are not parallel the other. Instead, docking slide (4050) is parallel first converging side (4014) of border (4010) for engaging first converging side (3014) of outermost brace (3010) of implant (3000) and docking slide (4052) is parallel second converging side (4016) of border (4010) for engaging second converging side of outermost brace (3010) of implant (3000).

Figure 3:
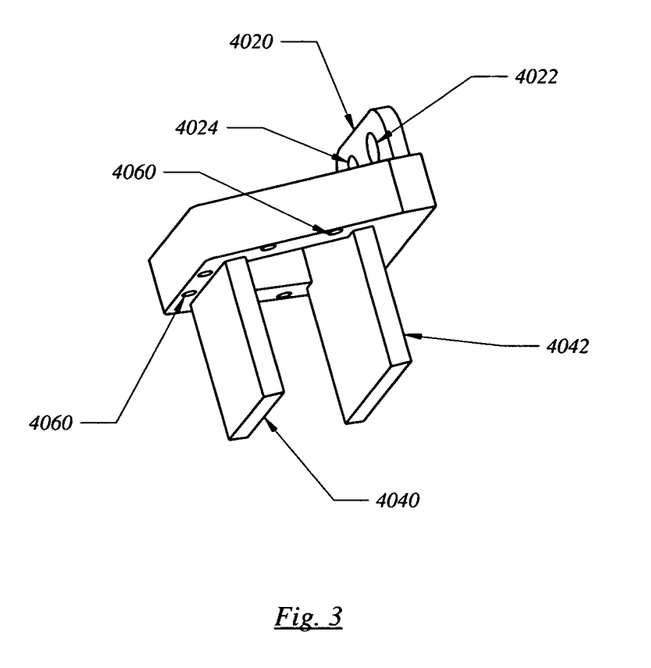
FIG. 3 is a perspective of a preferred embodiment of an implant facing side of a border of an end cap within the scope of the present invention.

FIG. 3 is a perspective of a preferred embodiment of an implant facing side of border (4010) of end cap (4000). Along with docking slides (4040) and (4042), implant facing side of border (4010) is provided with bores (4060) capable of aligning with spikes (3060) of cage (3000).

Figure 4:
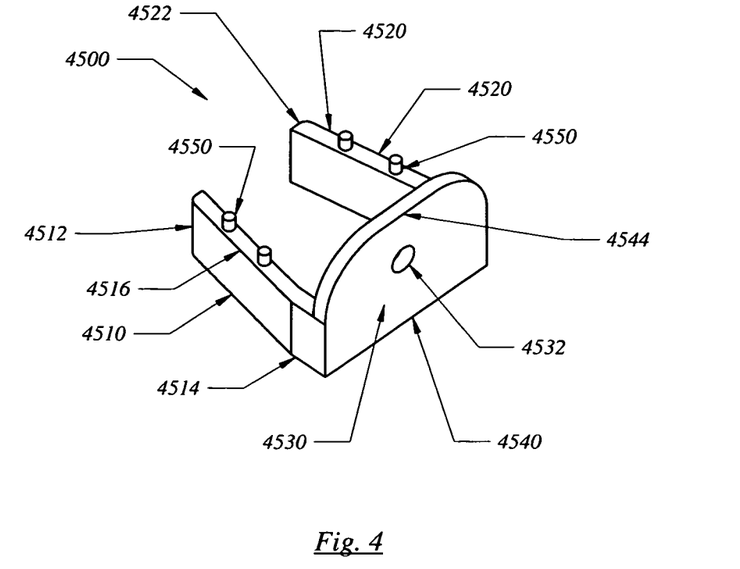
FIG. 4 is a perspective of a preferred embodiment of a connector capable of being positioned between the implant and the end cap.
Figure 5:
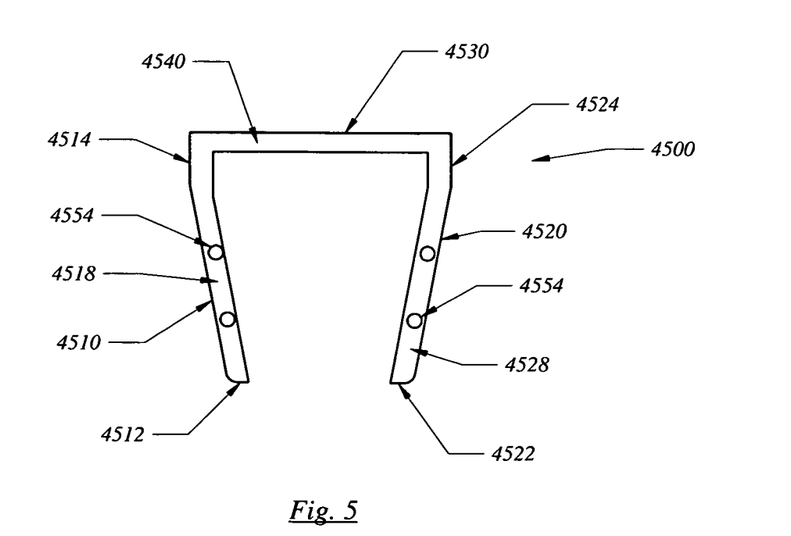
FIG. 5 is a plan view of a preferred embodiment of the coplanar margin of a connector.

FIG. 4 is a perspective of a preferred embodiment of a connector or extension (4500) capable of being positioned between cage (3000) and end cap (4000). Connector (4500) has first leg (4510) and second leg (4520). As shown in FIGS. 4 and 5, distal end (4512) of first leg (4510) and distal end (4522) of second leg (4520) converge toward the other. However, within the scope of the present invention, when engineering parameters require, first and second legs (4510 and 4520) can be parallel the other or diverging from the other. First side (4516) of first leg (4510) is provided with pins (4550) and first side (4526) of second leg (4520) is provided with pins (4550). Pins (4550) extend in a lengthwise direction away from biocompatible cage (3000).

Anterior section (4530) of connector or extension (4500) joins a first end (4514) of first leg (4510) and a second end (not shown in FIG. 4) of second leg (4520). Anterior section (4530), first leg (4510) and second leg (4520) share a coplanar margin (4540) that faces implant (3000). Anterior section (4530) is provided with a second margin (4544) opposite coplanar margin (4540) that extends in a longitudinal direction further away from biocompatible implant (3000) than pins (4550). In select preferred embodiments of extension (4000), anterior section (4530) includes hole (4532) capable of being engaged by a surgical tool (not shown in this view).

FIG. 5 is a plan view of coplanar margin (4540) of connector (4500). Second side (4518) of first leg (4510) and second side (4528) of second leg (4520) are provided with apertures (4554) capable of receiving spikes (3060) of biocompatible cage (3000).

Figure 6:
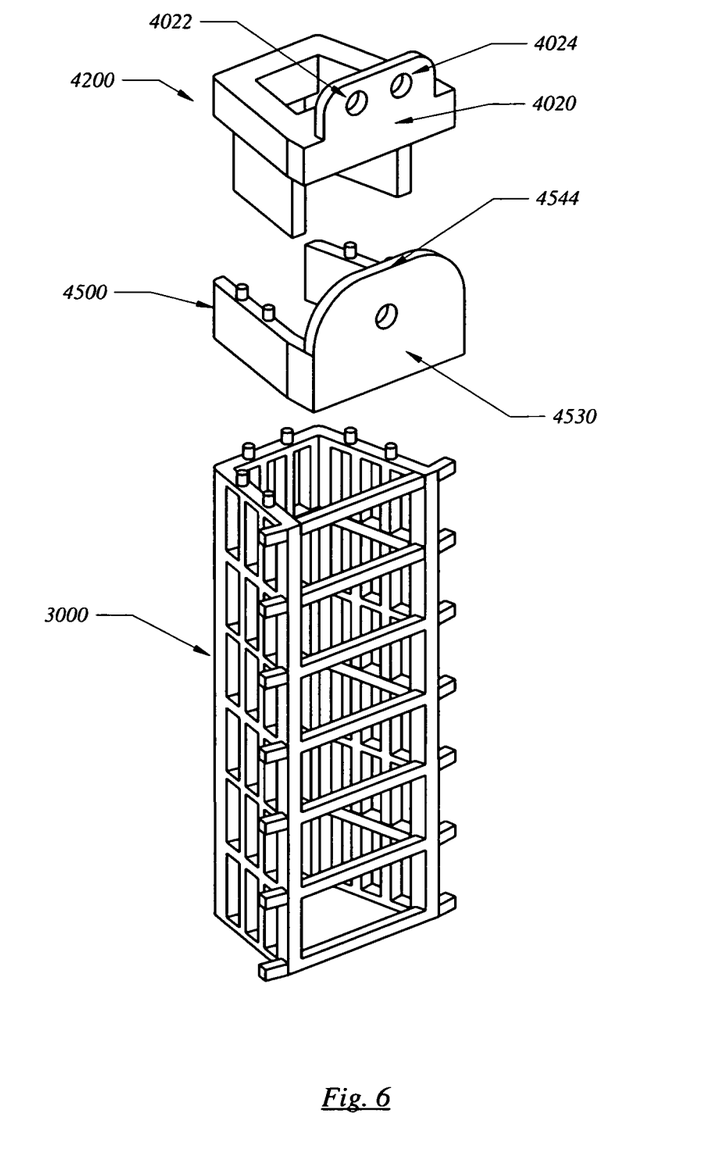
FIG. 6 is an exploded perspective of a preferred embodiment of the combination of a biocompatible cage, a connector and an end cap.
Figure 6A:
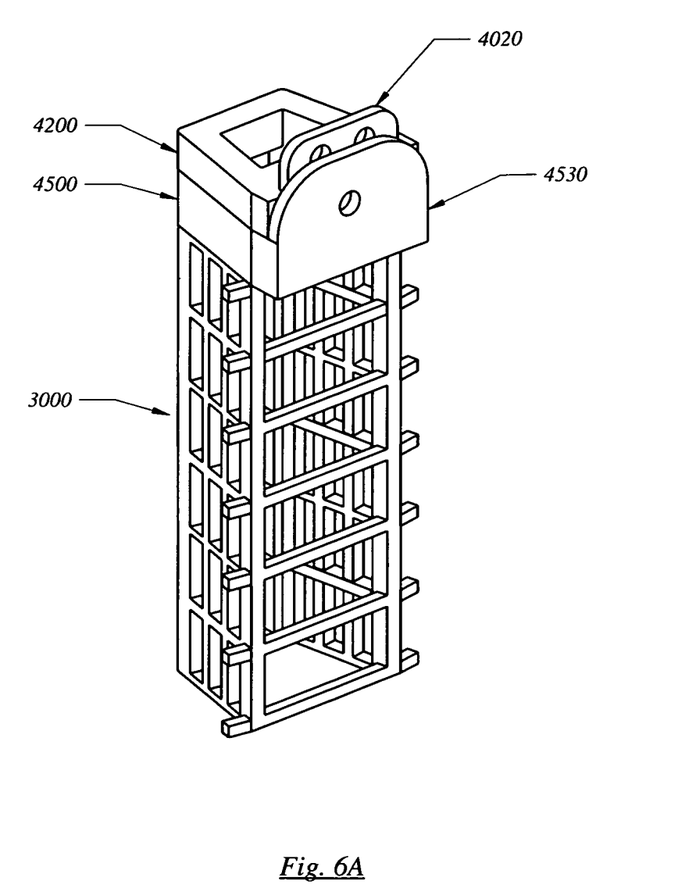
FIG. 6A is a perspective of a preferred embodiment of an engaged combination of the biocompatible cage, connector or extension and end cap.

FIG. 6 is an exploded perspective showing a preferred embodiment of the combination of biocompatible cage (3000), connector or extension (4500) and end cap (4200). FIG. 6A is a perspective showing a preferred embodiment of an engaged combination of biocompatible cage (3000), connector or extension (4500) and end cap (4200). When biocompatible cage (3000), connector (4500) and end cap (4200) are fully engaged within the surgical cavity, anterior section (4530) of connector (4500) is anterior to plate (4020) of end cap (4200). Second margin (4544) and anterior section (4530) of connector (4500) sufficiently cover openings (4022 and 4024) to prevent fasteners (not shown in this view) from backing out of plate (4020) of end cap (4200).

Having disclosed the invention as required by Title 35 of the United States Code, Applicant now prays respectfully that Letters Patent be granted for his invention in accordance with the scope of the claims appended hereto.

What is claimed is:

1. A combination capable of insertion about a surgically created cavity proximate to one or more vertebrae; said combination comprising:
    a) a biocompatible cage comprising
        a length having a longitudinal axis, a trapezoidal aperture spanning said length and two sides converging toward each other as said sides extend from anterior to posterior ends of said biocompatible cage said biocompatible cage; and
    b) an end cap comprising:
        i) a border comprising four sides;
        ii) a plate extending in said lengthwise direction parallel said longitudinal axis away from said biocompatible cage and comprising at least one opening for receiving a fastener; and
        iii) a pair of opposed generally flat docking slides docking with said trapezoidal aperture of said biocompatible cage.

2. The combination of claim 1 wherein:
    a) said biocompatible cage further comprises a plurality of spikes extending outwardly from said first end perimeter in said lengthwise direction; and
    b) said border of said end cap further comprises a first plurality of bores capable of aligning with some or all of said plurality of spikes.

3. The combination of claim 2 further comprising: a connector, capable of receiving said docking slides and positioned between said biocompatible cage and said end cap; said connector comprising:
    a) a first leg comprising:
        i) a plurality of apertures capable of aligning with some of said plurality of spikes; and
        ii) a plurality of pins capable of aligning with some of said plurality of bores; and
    b) a second leg comprising:
        i) a plurality of apertures capable of aligning with some of said plurality of spikes; and
        ii) a plurality of pins capable of aligning with some of said plurality of bores.

4. The combination of claim 3, wherein said connector comprises an anterior section joining a first end of said first leg and a first end of said second leg, wherein said anterior section shares a margin facing said biocompatible cage with said legs and includes an opposing margin extending further away from said biocompatible cage than said pluralities of pins, and wherein said anterior section is anterior to said plate.

5. A combination capable of insertion about a surgically created cavity proximate to one or more vertebrae; said combination comprising:
    a) a biocompatible cage comprising
        a length having a longitudinal axis
        and a trapezoidal aperture spanning said length; and
    b) an end cap comprising:
        i) a trapezoidal border; and
        ii) a plate extending in said lengthwise direction parallel said longitudinal axis away from said biocompatible cage and comprising at least one opening for receiving a fastener; and
        iii) opposed docking slides adapted to dock with said aperture of said biocompatible cage.

6. The combination of claim 5 wherein:
    a) said biocompatible cage further comprises a plurality of spikes extending outwardly from said first end perimeter in said lengthwise direction; and
    b) said border of said end cap further comprises a first plurality of bores aligning with some or all of said plurality of spikes.

7. The combination of claim 6 further comprising: a connector, capable of receiving said docking slides and positioned between said biocompatible cage and said end cap; said connector comprising:
    a) a first leg comprising:
        i) a plurality of apertures capable of aligning with some of said plurality of spikes; and
        ii) a plurality of pins capable of aligning with some of said plurality of bores; and
    b) a second leg comprising:
        i) a plurality of apertures capable of aligning with some of said plurality of spikes; and
        ii) a plurality of pins capable of aligning with some of said plurality of bores.

8. The combination of claim 7, wherein said connector comprises an anterior section joining a first end of said first leg and a first end of said second leg, wherein said anterior section shares a margin facing said biocompatible cage with said legs and includes an opposing margin extending further away from said biocompatible cage than said pluralities of pins, and wherein said anterior section is anterior to said plate.

9. An end cap for a biocompatible spinal implant; said end cap comprising:
    a) a border abutting a longitudinally positioned outermost brace of said biocompatible implant, wherein said outermost brace comprises an aperture;
    b) a plate comprising at least one opening for receiving a fastener; said plate positioned about an edge of said border and extending outward from said biocompatible spinal implant in a lengthwise direction parallel a longitudinal axis of said biocompatible implant; and
    c) a pair of opposed generally flat docking slides adapted to slidably engage inward sides of said longitudinally positioned outermost brace; wherein one of said pair of docking slides is wider than a second docking slide; wherein surfaces of said docking slides are without configurations preventing sliding removal of said docking slides from said biocompatible spinal implant; and wherein each said docking slide comprises a first surface engaging said outermost brace, a second corresponding surface opposite said first surface and a thickness between said first and said second surfaces.

10. The invention of claim 9, wherein an implant facing side of said border comprises a plurality of bores capable of engaging all or some spikes extending in said lengthwise direction from said brace.

11. The invention of claim 10, wherein said pair of opposed docking slides is configured to engage parallel inward sides of said longitudinally positioned outermost brace.

12. The invention of claim 10, wherein said pair of opposed docking slides is configured to engage converging inward sides of said longitudinally positioned outermost brace.

13. A combination capable of insertion about a surgically created cavity proximate to one or more vertebrae; said combination comprising:
    a) a biocompatible spinal implant comprising a longitudinally positioned outermost brace, wherein said outermost brace comprises a centralized aperture; and b) an end cap comprising:
  i) a border adapted to abut said longitudinally positioned outermost brace;
  ii) a plate comprising at least one opening for receiving a fastener; said plate positioned about an edge of said border and extending outward from said biocompatible spinal implant in a lengthwise direction parallel a longitudinal axis of said biocompatible implant; and
  iii) a pair of opposed docking slides adapted to engage inward sides, defined by said centralized aperture, of said longitudinally positioned outermost brace; wherein one of said pair of docking slides is wider than a second docking slide; wherein surfaces of said docking slides are without configurations preventing sliding removal of said docking slides from said centralized aperture and only said fastener prevents sliding removal of said docking slides from said centralized aperture; and wherein each said docking slide comprises a first planar surface engaging one of said inward sides and a thickness between a second surface and said first planar surface.

14. The combination of claim 13 further comprising a connector sandwiched between said end cap and said biocompatible spinal implant.

15. A combination capable of insertion about a surgically created cavity proximate to one or more vertebrae; said combination comprising:
  a) a spinal cage comprising a lengthwise end, wherein said lengthwise end comprises an aperture; and
  b) an end cap comprising:
    i) a border adapted to abut said lengthwise end of said spinal cage;
    ii) a plate comprising at least one opening adapted to receive a screw; said plate positioned about an edge of said border and extending outward from said spinal cage in a direction parallel a longitudinal axis of said spinal cage; and
    iii) a pair of opposed docking slides adapted to slidably engage inward sides of said lengthwise end of said spinal cage; wherein only said screw prevents unrestricted removal of said docking slides from said spinal cage, via said aperture; and wherein each said docking slide comprises a first surface engaging one of said inward sides and a thickness between a second surface and said first planar surface.

16. The of claim 15 further comprising a connector sandwiched between said end cap and said spinal cage.

17. A combination capable of insertion about a surgically created cavity proximate to one or more vertebrae; said combination comprising:
  a) a spinal cage comprising a lengthwise end, wherein said lengthwise end comprises an aperture; and
  b) an end cap comprising:
    i) a border adapted to abut said lengthwise end of said spinal cage;
    ii) a plate comprising at least one opening adapted to receive a fastener; said plate positioned about an edge of said border and extending outward from said spinal cage in a direction parallel a longitudinal axis of said spinal cage; and
    iii) a pair of opposed docking slides adapted to slidably engage, via said aperture, inward sides of said lengthwise end of said spinal cage; wherein surfaces of said docking slides are without configurations preventing sliding removal of said docking slides from said aperture, and wherein each said docking slide comprises a first planar surface engaging one of said inward sides.

18. The end cap and spinal cage of claim 17 further comprising a connector sandwiched between said combination.

* * * * *